(12) United States Patent
Murphy

(10) Patent No.: US 7,744,587 B2
(45) Date of Patent: Jun. 29, 2010

(54) SURFACE MODIFIED REINFORCING MEMBER FOR MEDICAL DEVICE AND METHOD FOR MAKING SAME

(75) Inventor: Richard F. Murphy, White Bear Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 506 days.

(21) Appl. No.: 10/667,909

(22) Filed: Sep. 22, 2003

(65) Prior Publication Data

US 2005/0061771 A1 Mar. 24, 2005

(51) Int. Cl.
*A61M 25/00* (2006.01)
(52) U.S. Cl. .................................. 604/527; 604/526
(58) Field of Classification Search .......... 604/524, 604/523, 525, 528; 600/381, 585; 264/171.2, 264/209.4
See application file for complete search history.

(56) References Cited

U.S. PATENT DOCUMENTS

| | | | |
|---|---|---|---|
| 5,244,619 A | 9/1993 | Burnham | |
| 5,330,521 A * | 7/1994 | Cohen | 607/122 |
| 5,338,295 A | 8/1994 | Cornelius et al. | |
| 5,549,109 A | 8/1996 | Samson et al. | |
| 5,568,218 A | 10/1996 | Dussinger et al. | |
| 5,569,218 A | 10/1996 | Berg | |
| 5,603,705 A | 2/1997 | Berg | |
| 5,674,208 A | 10/1997 | Berg et al. | |
| 5,680,873 A | 10/1997 | Berg et al. | |
| 5,733,248 A | 3/1998 | Adams et al. | |
| 5,762,631 A * | 6/1998 | Klein | 604/171 |
| 5,772,609 A | 6/1998 | Nguyen et al. | |
| 5,853,400 A | 12/1998 | Samson | |
| 5,860,963 A | 1/1999 | Azam et al. | |
| 5,911,715 A | 6/1999 | Berg et al. | |
| 6,139,510 A | 10/2000 | Palermo | |
| 6,159,187 A | 12/2000 | Park et al. | |

(Continued)

FOREIGN PATENT DOCUMENTS

EP  0 617 977  10/1994

(Continued)

OTHER PUBLICATIONS

U.S. Appl. No. 10/238,227, filed Sep. 10, 2002, Pu Zhou.

(Continued)

*Primary Examiner*—Nicholas D Lucchesi
*Assistant Examiner*—Christopher D Koharski
(74) *Attorney, Agent, or Firm*—Crompton, Seager & Tufte, LLC

(57) ABSTRACT

Medical devices, medical device components, and methods of making the same. For example, one embodiment provides a method of making a reinforcing member adapted and configured for use in a medical device. The method includes providing one or more structural elements adapted and configured for creating the reinforcing member, the one or more structural elements including a surface having a portion with an initial surface area, and treating at least the portion of the surface of the one or more structural elements to provide a final surface area that is greater than the initial surface area. The one or more structural elements are used in creating the reinforcing member. The reinforcing member can then be incorporated into the structure of the medical device.

11 Claims, 3 Drawing Sheets

U.S. PATENT DOCUMENTS

| | | | |
|---|---|---|---|
| 6,217,565 | B1 | 4/2001 | Cohen |
| 6,273,880 | B1 | 8/2001 | Berg et al. |
| 6,325,790 | B1 * | 12/2001 | Trotta ............... 604/523 |
| 6,416,389 | B1 | 7/2002 | Perry et al. |
| 6,464,889 | B1 * | 10/2002 | Lee et al. ............ 216/37 |
| 6,669,886 | B1 * | 12/2003 | Willard ............ 264/171.14 |
| 2001/0027310 | A1 * | 10/2001 | Parisi et al. ............ 604/524 |
| 2002/0098278 | A1 * | 7/2002 | Bates et al. ............ 427/2.1 |
| 2002/0143384 | A1 * | 10/2002 | Ozasa ............ 623/1.12 |
| 2003/0135198 | A1 | 7/2003 | Berhow et al. |

FOREIGN PATENT DOCUMENTS

| WO | WO 98/50098 | 11/1998 |
|---|---|---|
| WO | WO 02/11806 | 2/2002 |

OTHER PUBLICATIONS

U.S. Appl. No. 10/346,697, filed Jan. 17, 2003, Pu Zhou et al.

* cited by examiner

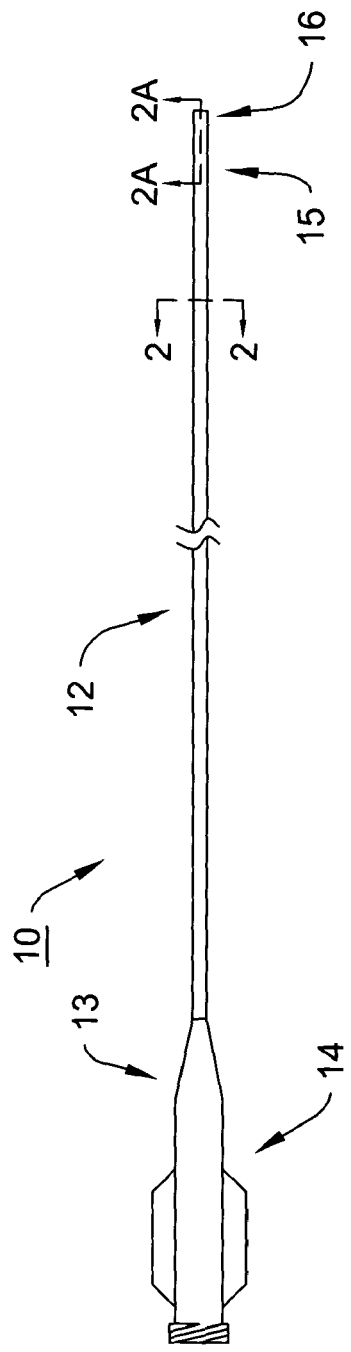
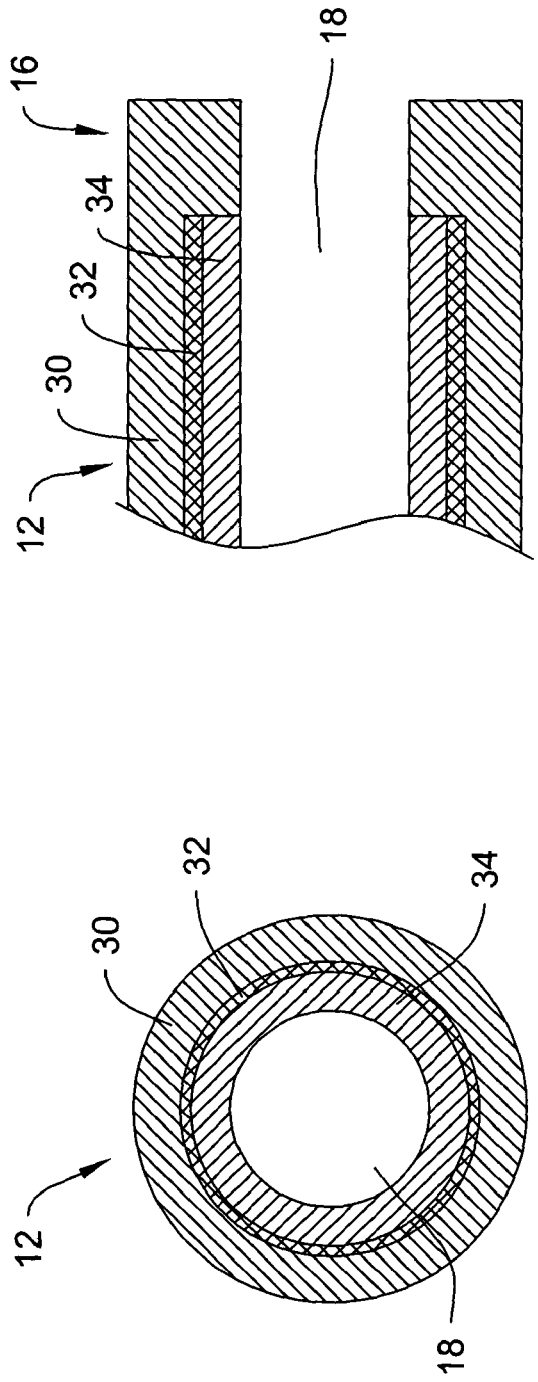
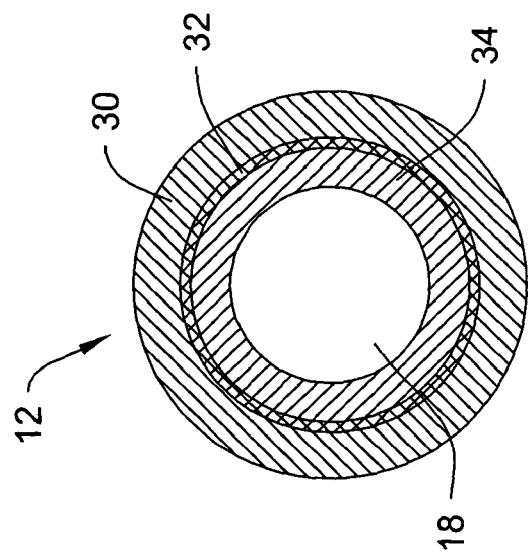

SURFACE MODIFIED REINFORCING MEMBER FOR MEDICAL DEVICE AND METHOD FOR MAKING SAME

FIELD OF THE INVENTION

The invention generally relates to medical devices. More specifically, the invention relates to reinforcing members for medical devices having a modified surface, and methods for producing the same.

BACKGROUND

It is generally known to provide reinforcing members for use in medical devices, such as intravascular guidewires, catheters, and the like. The prior art offers a number of different structures and mechanisms for incorporating reinforcing structures into medical devices. Each of these different structures and mechanisms has certain advantages and disadvantages. There is an ongoing need to provide alternative structures and mechanisms to help incorporate reinforcing structures in medical devices.

SUMMARY

The invention provides alternative designs and methods of making medical devices including reinforcing structures. At least some embodiments relate to modifying at least a portion of the surface of a reinforcing member, or the structural elements making up the reinforcing member, that is adapted and configured for use in a medical device. For example, one embodiment relates to a method of making a reinforcing member that includes treating at least the portion of the surface of one or more structural elements used to create the reinforcing member to provide increased surface area, or to provide a roughened or textured surface on at least a portion of the finished reinforcing member. Such a modified surface can provide certain beneficial characteristics, for example, better physical characteristics, or better connection between the reinforcing member and other components of the medical device. In some embodiments, one or more structural elements used to create the reinforcing member are treated prior to creating the finished reinforcing member, while in other embodiments, the completed reinforcing member is treated prior to incorporation into the medical device. Some other embodiments relate to a medical device and a method of making a medical device that includes such a reinforcement member.

The above summary of some embodiments is not intended to describe each disclosed embodiment or every implementation of the present invention. The Figures, and Detailed Description which follow more particularly exemplify these embodiments.

BRIEF DESCRIPTION OF THE FIGURES

The invention may be more completely understood in consideration of the following detailed description of various embodiments of the invention in connection with the accompanying drawings, in which:

FIG. 1 is a plan view of a medical device in accordance with one example embodiment of the invention, shown as a guide or diagnostic catheter;

FIG. 2 is a cross-sectional view taken along line 2-2 in FIG. 1;

FIG. 2A is a longitudinal sectional view taken along line 2A-2A in FIG. 1;

Figure 4:
FIG. 4 is a black and white photograph of a stainless steel filament adapted for use in a reinforcing braid shown at a magnification of 80× after treatment with a chemical etch.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention. Those skilled in the art and others will recognize that the invention can be manifested in a variety of forms other than the specific embodiments described and contemplated herein. Accordingly, departures in form and detail may be made without departing from the scope and spirit of the invention.

As indicated above, the invention provides alternative design, and methods of making medical devices including reinforcing structures. At least some example embodiments generally relate to a reinforcing member, and a method of making a reinforcing member, that is adapted and configured for use in a medical device, and that includes one or more surfaces, or portions thereof, that have been or are treated to provide, for example, increased surface area, or to include a roughened or textured portion. In some embodiments, one or more structural elements used to create the reinforcing member are treated prior to creating the finished reinforcing member, while in other embodiments, the completed reinforcing member is treated prior to incorporation into the medical device.

Such a reinforcing member can then be incorporated into a medical device. For example, in some embodiments, the reinforcing member is incorporated into the body of a medical device such as a catheter, guidewire, or the like, and the treated surface on the reinforcing member can provide beneficial properties, for example, for good connection, such as adhesion or bonding, of the reinforcing member with other components of the medical device. For example, in some embodiments, the surface modified reinforcing member can help to maintain a mechanical surface bond or interlocking bond with other components of the device.

Refer now to FIG. 1 which illustrates a medical device 10 in accordance with one example embodiment. In the embodiment shown, the medical device 10 is in the form of a guide or diagnostic catheter. Although set forth with specific reference to a guide or diagnostic catheter, in the example embodiments shown in the Figures and discussed below, the invention may relate to virtually any medical device including an elongate shaft or member having a reinforcing layer disposed therein. For example, the invention may be applied to medical devices such as a balloon catheter, an atherectomy catheter, a drug delivery catheter, a stent delivery catheter, an endoscope, an introducer sheath (if the sheath includes a reinforcing member), a fluid delivery device, other infusion or aspiration devices, device delivery (i.e. implantation) devices, and the like. Thus, while the Figures and descriptions below are directed toward a guide or diagnostic catheter, in other applications sizes in terms of diameter and length may vary widely, depending upon the desired properties of a particular device. For example, in some devices, lengths may range from about 1-300 centimeters or more, while outside diameters may range from about 1 F to about 20 F, or even more in some embodiments.

The guide or diagnostic catheter 10 may have a length and an outside diameter appropriate for its desired use, for example, to enable intravascular insertion and navigation. For example, the catheter 10 may have a length of about 100 cm-150 cm and an outside diameter of approximately 4 F-9 F, when catheter 10 is adapted as a guide catheter. The guide or diagnostic catheter 10 may include structure and materials that are substantially conventional except as described herein and shown in the drawings. While catheter 10 is described in terms of intravascular use, in other embodiments the guide or diagnostic catheter 10 may be suited for other uses in the digestive system, soft tissues, or any other use including insertion into an organism for medical uses.

The catheter 10 includes an elongate shaft 12 having a proximal end portion 13 and distal end portion 15. A distal tip 16 is connected to the distal portion 15 of the elongate shaft 12. The distal tip 16 and a distal portion 15 of the elongate shaft 12 may be curved as desired depending on the particular application. The elongate shaft 12 and the distal tip 16 include a lumen 18 extending there through to facilitate, for example, insertion of other medical devices (e.g., guide wires, balloon catheters, etc.) there through, and/or to facilitate injection of fluids (e.g., radiopaque dye, saline, drugs, etc.) there through. A manifold 14 is connected to the proximal end of the elongate shaft 12 to facilitate connection to other medical devices (e.g., syringe, Y-adapter, etc.) and to provide access to the lumen 18. In some embodiments, the catheter 10 may exclude the lumen, or may include additional devices such as inflation or anchoring members, sensors, optical elements, ablation devices or the like. In some embodiments, the catheter 10 may be significantly shorter and used as an introducer sheath, for example, while in other embodiments the catheter 10 may be adapted for other medical procedures.

As best seen in FIGS. 2 and 2A, the elongate shaft 12 may be multi-membered or multi-layered. In the illustrative embodiment, the elongate shaft 12 may include an outer member or layer 30, a reinforcement member or layer 32, an inner member or layer 34, and a distal tip 16. It should be understood that more or fewer members or layers can be used depending upon the desired characteristics of the device. Furthermore, while an outer layer 30 and inner layer 34 are described with respect to the particular embodiment, these layers 30, 34 may be provided as a single layer into which a reinforcement member or layer 32 is later embedded, for example. The inner layer 34 and outer layer 30 may be provided to physically be a single layer with the reinforcement layer 32 providing an "imaginary" dividing line between inner layer 34 and outer layer 30. The distal tip 16 may comprise the outer layer 30 extending beyond the inner layer 34 and the reinforcement layer 32 to define a tip, for example, a soft atraumatic tip. In other embodiments the distal tip 16 may be attached to the rest of catheter 10 in a separate fabrication step.

Inner layer 34 and outer layer 30 may be made of any suitable material and by any suitable process, the materials and processes varying with the particular application. Examples of some suitable materials include, but are not limited to, polymers such as polyoxymethylene (POM), polybutylene terephthalate (PBT), polyether block ester, polyether block amide (PEBA), fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), polyether-ester, polymer/metal composites, etc., or mixtures, blends or combinations thereof, and may also include or be made up of lubricous polymers. One example of a suitable polyether block ester is available under the trade name ARNITEL, and one suitable example of a polyether block amide (PEBA) is available under the trade name PEBAX®, from ATOMCHEM POLYMERS, Birdsboro, Pa.

The inner layer 34 may include a lubricious polymer such as HDPE or PTFE, for example, or a copolymer of tetrafluoroethylene with perfluoroalkyl vinyl ether (PFA) (more specifically, perfluoropropyl vinyl ether or perfluoromethyl vinyl ether), or the like. The outer layer 30 may include a flexible polymer such as polyether block amide or polyether-ester elastomer. The outer layer 30 may be formed, for example, by extrusion, co-extrusion, interrupted layer co-extrusion (ILC), or fusing several segments end-to-end. The outer layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

In some embodiments, the material of the inner layer 34 and/or outer layer 30 can be blended with a liquid crystal polymer (LCP). For example, the mixture can contain up to about 5% LCP. This has been found to enhance torqueability.

A lubricious, a hydrophilic, a protective, or other type of coating may be applied over portions or all of the shaft 12. Hydrophobic coatings such as fluoropolymers provide a dry lubricity which improves guidewire handling and device exchanges. Lubricious coatings can aid in insertion and steerability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

Figure 5:
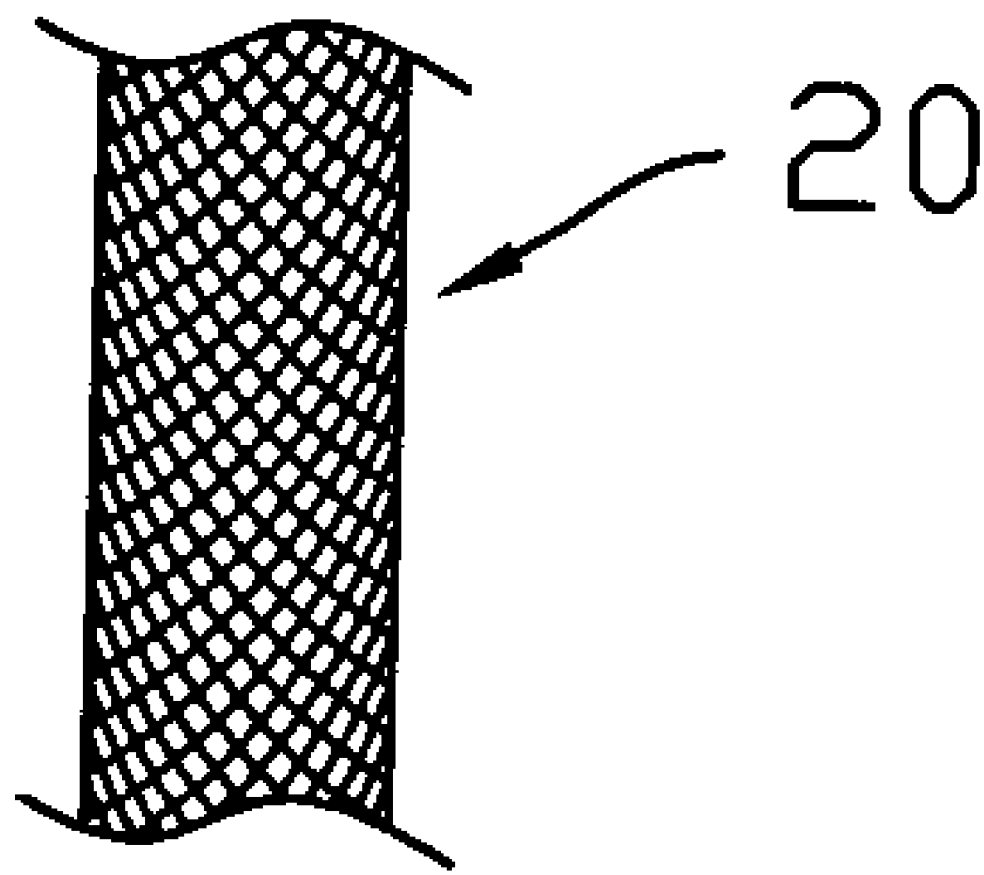
FIG. 5 is a partial side view of a reinforcing braid that may be used, for example, in some example embodiments.

The reinforcement member or layer 32 may comprise any structure that would be suited for use in the particular medical device into which it will be incorporated. In some embodiments, the reinforcement layer 32 may comprise one or more structural elements that are used to create the reinforcing member or layer 32. For example, the reinforcement layer 32 may comprise a braid of a plurality of interwoven strands, a coil of one or more strands or fibers, a mesh of fibers or strands, one or more wires, a fabric of fibers or strands, one or more filaments, one or more tubular member that can be either solid, or include one or more openings or apertures there through, or combinations thereof, and other like structure or structures. In the embodiment shown, the reinforcement layer 32 can include a braid of interwoven strands, for example a braid 20 as shown in FIG. 5. referring back to FIGS. 1-2A, the reinforcing member 32 can be of any appropriate size and shape for use in the particular medical device into which it will be incorporated. As shown in FIG. 2, the reinforcing member 32 illustrated has a generally circular cross-sectional shape, and is appropriately sized for use in an intravascular catheter. A broad variety of other shapes and sizes could be used, depending upon the intended use and desired characteristics of the reinforcing member 32. For example, in some embodiments, the reinforcing member 32 could have a flat, curved, oval, or multisided cross-sectional shape, for example, triangular, square, rectangular, pentagonal, hexagonal, and so fourth.

Furthermore, the reinforcing member 32 can be formed using any suitable technique for forming the appropriate reinforcing structure. For example, a braid can be formed using a suitable number of strands or filaments. The number of strands or filaments used in such a braided reinforcing member 32 will often depend upon the desired characteristics of the braid, and the patterns or techniques used to form the braid. In some embodiments, between one and thirty-two, or even more, strands may be used in each direction. In some embodiments, the braid reinforcement layer can include an equal number of strands wound in each direction at the same pitch. In other words, the same number of strands are wound in opposite directions at the same pitch. Some other embodiments may include a braid reinforcement layer with an unequal number of strands wound in each direction. The strands in each direction may be wound at the same pitch or at differing pitches. In some such embodiments, the shaft can include increased contact surface area between the inner layer 34 and the outer layer 30, which can provide for enhanced the adhesion between the inner layer 34 and the outer layer 30 to thereby improve the structural integrity of the catheter shaft and provide improved performance, for example, relative to some prior art shafts. Some examples of structures of reinforcing members can be found in U.S. patent application Ser. No. 10/346,697, filed on Jan. 17, 2003, entitled "Unbalanced Reinforcing Members for Medical Device", which is incorporated herein by reference. The braid density may also vary widely; in some embodiments, the braid density may be as low as about 10 pic; while in other embodiments braid density may increase to the range of about 300 pic.

The strands or filaments or other structures should be appropriately sized and shaped depending upon the desired characteristics of the braid or other reinforcing structure used. In some embodiments, the cross-sectional shape of the filaments or strands can be circular, oval, or multisided, for example, triangular, square, rectangular, pentagonal, hexagonal, and so fourth. In other embodiments, the filaments may be formed as ribbons.

The reinforcement layer 32, or the strands or fibers or other structural elements making up the reinforcing layer 32, may include or be made of any suitable material. Some examples of suitable materials can include, for example, polymers, metal-polymer composites, metals, metal alloys, or the like, or combinations or mixtures thereof. At least a portion of the reinforcing member 32, or at least some of the filaments or strands making up the reinforcing member 32, can be made of a metallic material, polymeric material, or combinations thereof. In some embodiments or application, suitable metallic materials include, for example, those that can be annealed into a desired shape. Some examples of metallic materials include stainless steel, tungsten, nickel, cobalt, titanium, gold, iridium, or alloys thereof including, for example, nickel-titanium alloy, such as linear elastic or superelastic nitinol, nickel-chromium alloy, nickel-chromium-iron alloy, as well as other such metallic materials, or combinations thereof. Some particular examples of suitable stainless steel alloys include especially high tensile grades, and/or other grades such as 304 and 440A and 440C stainless steel alloys, as well as alloys containing titanium. In some example embodiments, the reinforcing member is a reinforcing braid adapted and configured for use in an intravascular catheter and is formed with primarily stainless steel filaments. For additional embodiments, suitable polymeric materials also include those that can be annealed into a desired shape. Some examples of suitable polymers include nylon, polyesters, acrylics and combinations of mixtures thereof. The strands may also comprise non-metal materials such as liquid crystal polymer (LCP) fibers, glass fibers, etc.

In some embodiments, the reinforcing member 32 includes combinations of filaments or strands or other such structures made up of different types of materials. For example, in some particular example embodiments, the reinforcing member 32 is a reinforcing braid formed with a combination of stainless steel filaments and tungsten filaments.

At least a portion of a surface of the reinforcement member or layer 32, or at least a portion of a surface of the one or more structural elements making up the reinforcing member or layer 32, are treated, either prior to, or after formation of the reinforcing member 32 to provide for a modified surface. The modified surface, or portions thereof, provide, for example, increased surface area relative to the surface prior to treatment. Additionally, in at least some embodiments, the modified surface, or portions thereof, provide, a roughened or textured surface relative to the surface prior to treatment. Such a modified surface can provide for beneficial properties. For example, a reinforcement member or layer 32, or the one or more structural elements thereof, that include a treated surface having greater surface area, or including a roughened or textured surface can provide for better bonding with other structural elements of the medical device. For example, this design allows improved connection or adhesion between, for example, the inner layer 34 and the reinforcing member 32, and/or between the outer layer 30 and the reinforcing member 32.

Treatment of a surface of the reinforcement member or layer 32, or at least a portion of a surface of the one or more structural elements making up the reinforcing member or layer 32, can occur using any of a broad variety of methods or techniques that would provide the treated surface with the desired properties, for example, increased surface area or a roughened or textured surface. In some embodiments, methods such as chemical etching or treatment, plasma etching or treatment, corona etching or treatment, mechanical etching or treatment, or the like can be used.

One example of chemical etching includes using an acid etch solution to treat the surface of the reinforcing member, or the surface of the one or more structural elements making up the reinforcing member 32. Some examples of suitable acid etch solutions include, for example, solutions including $FeCl_3$, HCl, HF, or the like. Such techniques can be useful for example in treating metal surfaces, for example stainless steel or nitinol surfaces.

Figure 3:
FIG. 3 is a black and white photograph of a stainless steel filament adapted for use in a reinforcing braid shown at a magnification of 80× prior to treatment with a chemical etch.

For example, refer to FIGS. 3 and 4, which are black and white photographs of a stainless steel filament adapted for use in a reinforcing braid shown at a magnification of 80×. FIG. 3 shows the filament prior to treatment with a hydrochloric acid solution etch, while FIG. 4 shows the filament after treatment with a hydrochloric acid solution etch. As is shown by the photographs in FIGS. 3 and 4, acid etch provides the surface of the filament with an increased surface area and a roughened or textured surface. The filament can then be incorporated into a reinforcing member, such as a braid, and provide for better bonding with other structural elements of the medical device.

As suggested above, plasma treatment, corona treatment, or the like, may also be used to treat the surface of the surface of the reinforcement member or layer 32, or at least a portion of a surface of the one or more structural elements making up the reinforcing member or layer 32.

Also as suggested above, mechanical working can be used to treat the surface of the reinforcement member or layer 32, or at least a portion of a surface of the one or more structural elements making up the reinforcing member or layer 32. Mechanical methods can include techniques such as grinding, roughening, sanding, particle blasting, microabrasion treatment, such as with aluminum oxide ($Al_2O_5$) or other abrasive materials, and the like, to provide the treated surface with the desired properties, such as increased surface area, or a roughened or textured surface.

After treatment, the reinforcement member or layer 32 can be incorporated into a medical device. In embodiments where the one or more structural elements were treated prior to construction of the reinforcement member or layer 32, such elements can be used to create a reinforcement member or layer 32, which can then be incorporated into a medical device. Furthermore, the reinforcing member can be formed into a desired shape. It will be understood by those of skill in the art and others that any of a broad variety of techniques or structures can be used to bias the reinforcing member into the desired shape. Some examples of techniques used to shape reinforcing members are disclosed in U.S. patent application Ser. No. 10/238,227, filed on Sep. 10, 2002, entitled "SHAPED REINFORCING MEMBER FOR MEDICAL DEVICE AND METHOD FOR MAKING THE SAME" which is incorporated herein by reference. The medical device can be created using any appropriate technique used for construction of the particular device.

For example, referring back to FIGS. 1-2A, the elongate shaft 12 can be constructed using any appropriate technique, for example, by extrusion, a heat bonding process, casting, molding, and the like. For example, in one embodiment braid 32 may be formed over the inner layer 34, which may be supported by a removable mandrel, after which the outer layer 30 may be placed thereon. In some embodiments of the unique surface of the reinforcing member, or the one or more structural elements making up the reinforcing member or layer 32, described herein, the contact surface area between the inner layer 34 and the reinforcing member 32 and between the outer layer 30 outer layer and the reinforcing member 32 is increased relative to conventional designs. This design allows improved connection or adhesion between inner layer 34 and the reinforcing member, and improved connection or adhesion between outer layer 30 the reinforcing member. The enhanced connection between the inner layer 34 and the reinforcing member 32 and/or the outer layer 30 and the reinforcing member 32 may increase structural integrity of the shaft 12 and thereby provide improved performance in terms of torque response and kink resistance and curve performance. For some embodiments, the inner layer 34 and/or outer layer 30 may be excluded.

Some other examples of suitable catheter shaft constructions and materials can be found in U.S. Pat. Nos. 5,569,218; 5,603,705; 5,674,208; 5,680,873; 5,733,248; 5,853,400; 5,860,963; and 5,911,715, all of which are incorporated herein by reference.

The medical device can be curved or shaped as desired utilizing a broad variety of techniques. For example, catheters, such as guide catheters, can include a variety of shapes specific for different bodily passages and procedures. The stabilization of a catheter's position within a patient's anatomy is often achieved through curves or bends imparted into shaft. These pre-formed curves act by anchoring a selected portion of shaft against an opposing wall within a patient's vasculature or other body portion. Proper anchoring is often achieved by matching the predisposed shape of the curved shaft with the general curved anatomical shape around a targeted site. In vascular procedures involving treatment to one of the coronary arteries, often a curve is imparted proximate the distal portion of shaft with the intention of placing the catheter's distal tip at a desired angle. In embodiments medical devices that are designed for a procedure in a coronary artery, for example, shaft can be shaped so that when it is inserted through the aorta of the patient, the curvature of shaft will place distal tip at an angle that engages one of the coronary ostia. Those of skill in the art recognize some different shapes by names such as Judkins Right, Judkins Left, Amplatz Right, Amplatz Left, Bentson, Shepherd Hook, Cobra, Headhunter, Sidewinder, Newton, Sones and others, each formed in a different shape.

Having thus described some example embodiments of the invention, those of skill in the art will readily appreciate that other embodiments may be made and used within the scope of the invention. Numerous advantages of the invention covered by this document have been set forth in the foregoing description. It will be understood, however, that this disclosure is, in many respects, only illustrative. Changes can be made in details, particularly in the manner of size, shape, and arrangement of parts without exceeding the scope of the invention. Additionally, changes can be made in details with regard to order of steps and performing methods and other arrangements in accordance with the invention. The invention's scope is, of course, defined in the language of the claims.

What is claimed is:

1. A medical device including a reinforcing member, the medical device formed by the following process:
   providing one or more metallic filaments adapted and configured to be made into the reinforcing member for the medical device, the one or more metallic filaments including a metallic surface having a portion with an initial surface area, wherein the reinforcing member is a braid;

treating at least the portion of the surface of the one or more metallic filaments to provide a final surface area that is greater than the initial surface area;

creating the reinforcing member using the one or more metallic filaments; and incorporating the reinforcing member into the construction of the medical device, wherein the one or more metallic filaments each have a thickness and wherein the portion extends along each of the one or more metallic filaments for a length that is at least twice the thickness of the filament and wherein the portion encircles the metallic filament for the length, wherein the portion has a profile that is constant along the length, wherein other structural elements that have not undergone the treating step are also used in creating the braid.

2. The medical device of claim 1, wherein the medical device is a catheter.

3. The medical device of claim 1, wherein the reinforcing member includes an outer surface, an inner surface, and a lumen extending there through.

4. The medical device of claim 3, wherein incorporating the reinforcing member into the construction of the medical device includes connecting an outer layer to the outer surface of the reinforcing member.

5. The medical device of claim 4, wherein the outer layer comprises a polymer material.

6. The medical device of claim 3, wherein incorporating the reinforcing member into the construction of the medical device includes connecting an inner layer to the inner surface of the reinforcing structure.

7. The medical device of claim 6, wherein the inner layer comprises a polymer material.

8. The medical device of claim 1, wherein a plurality of the one or more metallic filaments each have a diameter and wherein the diameter of each of the plurality of metal filaments is constant along the portion subsequent to the treating step.

9. A medical device including a reinforcing member, the medical device formed by the following process:

providing one or more metallic filaments adapted and configured to be made into the reinforcing member for the medical device;

treating the surface of each of the one or more metallic filaments to roughen the surface and increase the surface area of the surface;

subsequent to the treatment step, forming a braid using the one or more metallic filaments; and incorporating the braid into the construction of the medical device, wherein other structural elements that have not undergone the treating step are also used in creating the braid.

10. The medical device of claim 9, wherein the step of incorporate the braid into the construction of the medical device includes the steps of providing a first polymeric layer having an outer surface and connecting the outer surface of the first polymeric layer directly to the braid.

11. The medical device of claim 9, wherein the step of incorporate the braid into the construction of the medical device includes the steps of providing a second polymer layer having an inner surface and connecting the inner surface of the second polymeric layer directly to the braid.

* * * * *